United States Patent [19]

Rutherford

[11] Patent Number: 4,625,557
[45] Date of Patent: Dec. 2, 1986

[54] ACOUSTICAL IMAGING SYSTEM

[75] Inventor: Jerry Rutherford, Anaheim, Calif.

[73] Assignee: Rutherford Scientific, Anaheim, Calif.

[21] Appl. No.: 703,315

[22] Filed: Feb. 20, 1985

[51] Int. Cl.⁴ .............................................. G01N 29/04
[52] U.S. Cl. ...................................................... 73/635
[58] Field of Search ................... 73/635, 637, 638, 639

[56] References Cited

U.S. PATENT DOCUMENTS

| | | | |
|---|---|---|---|
| 3,798,961 | 3/1974 | Flambard et al. | 73/637 |
| 3,844,164 | 10/1974 | Romere | 73/637 |
| 4,541,064 | 9/1985 | Livingston | 73/637 |

Primary Examiner—Anthoney V. Ciarlante
Attorney, Agent, or Firm—James F. Kirk

[57] ABSTRACT

An imaging system for non-destructively imaging the cross-section of a workpiece is taught. The image provided portrays the cross-section of the workpiece taken orthogonal to the surface of the workpiece along an operator selected course on the surface. The imaging system comprises: a scanner means for transmitting and receiving acoustical signals and for providing distance increment signals; a transmit and receive control means responsive to each distance increment signal for providing an acoustical drive signal and a column clock signal set. A sampling means is provided that is responsive to the column clock signal set for converting each the echo signal into a corresponding column series of digital values, each value characterizing the amplitude of the echo signal at time corresponding to a respective column clock signal within the echo interval. A storage means is provided for storing each column series of digital values as successive column arrays to form an image array of digital values. The storage means also reads and maps the image array of digital values as display data onto a video monitor.

19 Claims, 8 Drawing Figures

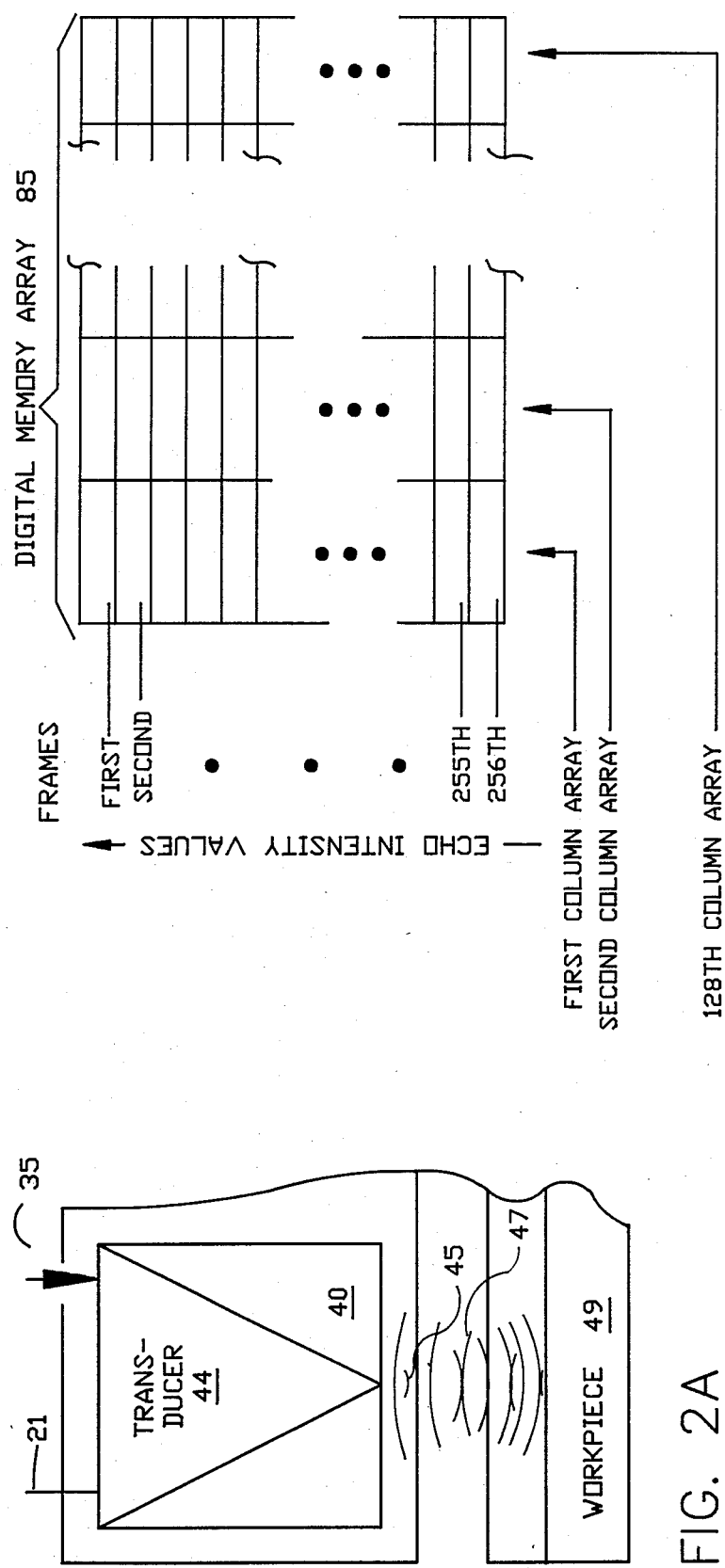
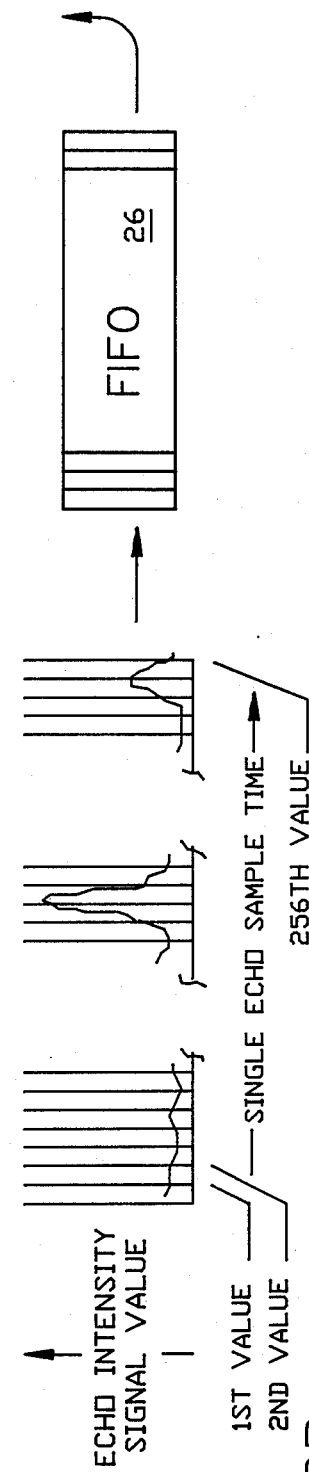
FIG. 2A
FIG. 2B

ACOUSTICAL IMAGING SYSTEM

BACKGROUND OF THE INVENTION

1. Field of the Invention

This invention relates to the field of Imaging Systems and more particularly to the field of instruments used for non-destructively measuring the thickness of a workpiece fabricated from material such as metal. This invention also relates to the field of portable instruments and most particularly to the field portable instruments used for measuring the thickness of metal and for detecting voids or hidden discontinuities impossible to observe without obtaining access to both surfaces of the workpiece. Typical workpieces are meant to include those such as common steel pipe lengths conventionally found as welded segments in industrial chemical and petroleum related industries.

2. Description of the Prior Art

Presently known non-destructive thickness measurement instruments typically employ X-Ray techniques or mechanical methods that require access to both surfaces of the workpiece under inspection. The invention system characterize an instrument system that does not require access to both sides of the workpiece and that permits an operator to use a hand held scanner and to manually scan a single surface of a workpiece while visually monitoring the imaged cross section of the workpiece for cracks or variations in thickness.

SUMMARY OF THE INVENTION

It is a major object of this invention to teach a system that is able to nondestructively image the cross-section of a workpiece formed from materials such as metal, plastic, ceramic or even fiber material such as paper or wood. The invention has particular utility in fields requiring the examination of steel pipe and structures.

It is another object of this invention to permit an operator to use a small hand held scanner to manually scan the outer surface of a workpiece without access to the inner or far surface of the workpiece. The operator obtains an immediate visual characterization of the cross-section of the workpiece on a video monitor eliminating the expense and delay typically associated with X-Ray related apparatus.

These and other objectives are realized in the invention acoustical imaging system for non-destructively imaging the cross-section of a workpiece, the cross-section being taken substantially orthogonal to the surface of the workpiece along an operator selected course on the surface. The image system comprises the following elements: a scanner means; a transmit and receive control means; storage means; a display means 50 and sampling means 20.

The scanner means provides a series of acoustical pulses in response to a corresponding series of acoustical drive signals for receiving reflected acoustical waves from the workpiece surface. The scanner means also provides an echo signal corresponding to the received acoustical waves for each acoustical pulse. It also provides a series of distance increment signals at substantially equal incremental distances in response to motion of the scanner means on the workpiece surface along the operator selected course.

The transmit and receive control means 30 is responsive to each distance increment signal for providing an acoustical drive signal and a column clock signal set comprising a predetermined number of consecutive spaced column clock signals. The duration of the column clock signal set characterizing an echo interval as the time required for the acoustical waves resulting from each acoustical pulse to move through the workpiece and return to the scanner means;

The sampling means 20 is responsive to the column clock signal set for converting each the echo signal into a corresponding column series of digital values. Each digital value characterizes the amplitude of the echo signal at a time corresponding to a respective column clock signal within the echo interval.

The storage means 90 stores each column series of digital values as successive column arrays to form an image array of digital values. Each digital value has a corresponding column and row address.

The display means 50 forms an image from the display data. The display data is formed from the image array of digital values, each digital value controlling the gray scale level of a pixel on the image, the image characterizing the cross-section of the workpiece.

In this embodiment of the imaging system, the scanner means 15 further comprises an encoder means 46 that has at least one roller in contact with the the workpiece surface for translating linear motion along the operator selected course into an angular signal to the encoder. The encoder means is responsive to the angular signal for providing the distance increment signals to the transmit and receive control means.

The transducer means 44 is responsive to the acoustical drive signals and provides acoustical pulses. These pulses provide echo signals in response to the reflected acoustical waves.

In an alternative embodiment of the imaging system, the encoder means further comprises a rotary switch having a rotary shift rotateably coupled to the roller. The rotatable switch provides the distance increment signals at uniform distance increments along the operator selected course in response to roller rotation induced by roller contact with the workpiece surface and in response to movement of the scanner means on the operator selected course.

In this alternative embodiment, the transducer means is further characterized to focus the acoustical energy in each acoustical pulse into a relatively narrow wedge shaped beam.

In an alternative embodiment, the transducer means is further characterized to comprise a first transducer responsive to the acoustical drive signals to provide acoustical pulses and a second transducer is included to be responsive to the reflected acoustical waves for providing the echo signals.

In yet another alternative embodiment, the transmit and receive control means has a transmit control circuit 32 that is responsive to the distance increment signals from the scanner means. It provides an acoustical drive transmit signal in response to each distance increment signal and it provides an echo interval signal. Each echo interval signal is generated after a first delay interval measured from the start of each acoustical drive transmit signal In this alternative embodiment, a pulse circuit having a high output pulse power capability such as pulser circuit 34 is responsive to the transmit signal to provide the acoustical drive signals. The pulser circuit is characterized to control the amplitude, shape and duration of the acoustical drive signal.

The sample rate timing circuit 38 is coupled to receive the echo interval signal and provides column clock signal set.

BRIEF DESCRIPTION OF THE DRAWINGS

The invention will further be described as to an illustrative embodiment in conjunction with the accompanying drawings in which:

FIG. 2A is a block diagram of the scanner means and workpiece showing a schematic representation of the acoustical pulse and echo.

FIG. 2B is a graph showing echo intensity versus echo sample time and showing movement of the intensity values to the FIFO and thence into the digital memory array locations.

FIGS. 4b, 4c and 4d are sectional views taken on FIG. 4a.

DESCRIPTION OF THE PREFERRED EMBODIMENT

Figure 1:
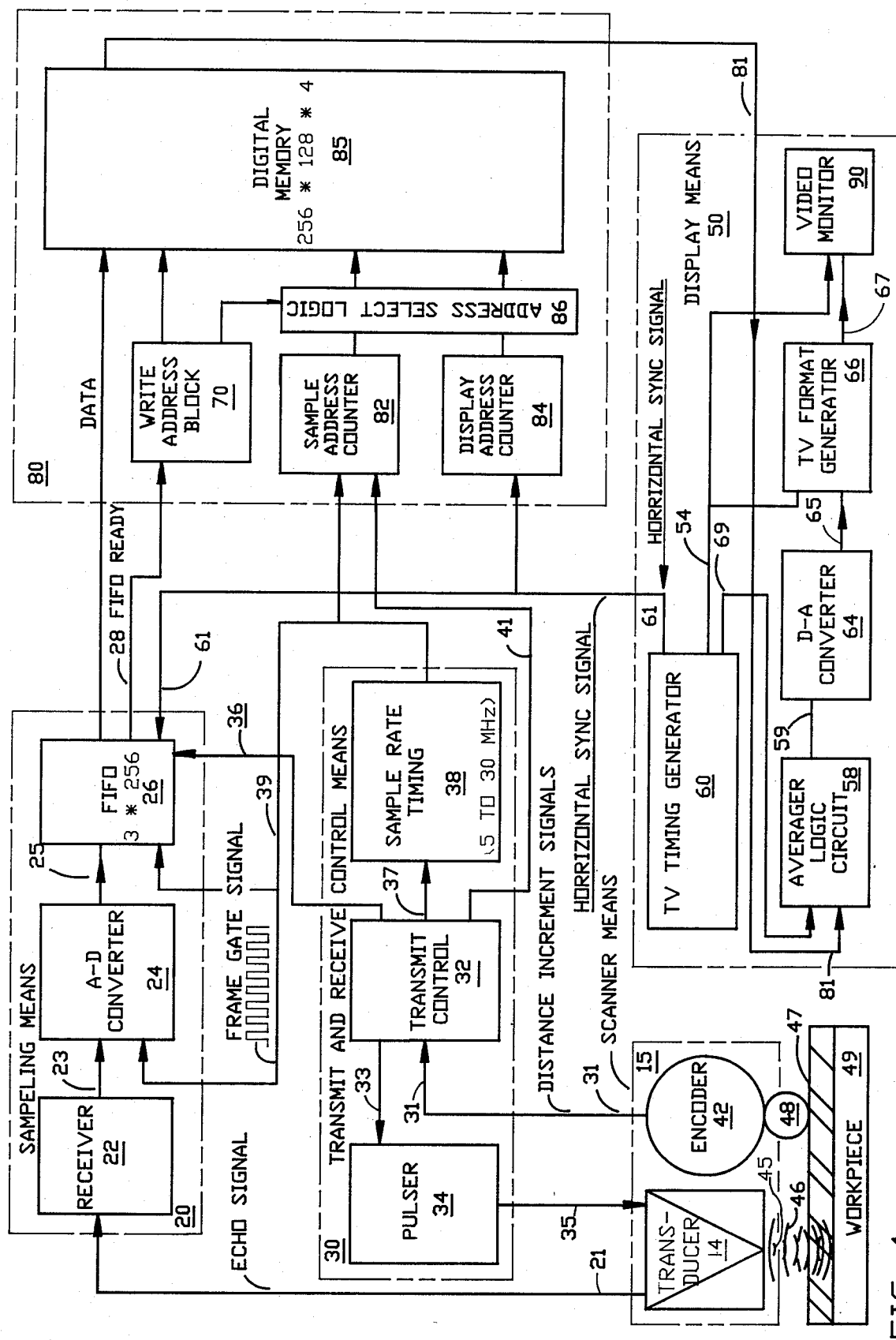
FIG. 1 is a block diagram of a preferred Embodiment of the invention acoustical imaging system.

In accordance with the present invention, FIG. 1 shows a block diagram of the acoustical imaging system 10 for non-destructively imaging the cross-section of a workpiece 49. The cross-section is taken substantially orthogonal to the surface of the workpiece along an operator selected course on the surface of the workpiece. The preferred embodiment of the invention contains major elements shown in the block diagram of FIG. 1 in phantom boxes. These elements include scanner means 15, transmit and receive control means 30, sampling means 20, memory means 100 and display means 50.

The scanner means 15 provides a series of acoustical pulses in response to a corresponding series of acoustical drive signals delivered to the scanner means on control line 35. The scanner means 15 also receives reflected acoustical waves from the workpiece surface 47. The scanner means provides an echo signal on signal line 21 that corresponds to the received acoustical waves such as 46 for each acoustical pulse. The scanner means 15 also provides a series of distance increment signals on signal line 31 at substantially equal incremental distances along the workpiece path chosen by the operator in response to motion of the scanner means on the workpiece surface along the operator selected course.

The transmit and receive control means within phantom block 30 is responsive to each distance increment signal on signal line 31. It provides an acoustical drive signal on signal line 33 with the arrival of each distance increment signal on signal line 31. The transmit and receive control means also provides a column clock signal set of a predetermined number of consecutive spaced column clock signals, such as 256. The duration of the column clock signal set characterizes such as that shown in FIG. 2B residing between the first value and the 256th value segments. The echo interval is the time required for the acoustical waves resulting from each acoustical pulse 45 to move through the workpiece and return such as 46 to the scanner means.

The sampling means characterized by phantom block 20 is responsive to the column clock signal set on signal line 39 for converting each the echo signal on signal line 21 into a corresponding column series of digital values. Each of the digital values characterizes the amplitude of the echo signal at time corresponding to a respective column clock signal within the echo interval.

The elements within phantom block 90 characterize a storage means 90 for storing each column series of digital values as successive column arrays to form an image array of digital values. FIG. 2B shows a pictorial representation of column arrays within the digital memory array 85. Each location or address within the array is located via a row and column address. Each digital value has a corresponding column and row address and each address location is addressable for reading or writing. The digital value in each cell or address location is read and put out as display data on signal line 81. The image array stored as digital values within the memory means 100 is read as display data in a display compatible format;

The display means is characterized by the elements within phantom block 50. The display means forms an image from the display data when the display data is converted to a video signal and displayed on a video monitor. The image is formed from the data formed from the image array of digital values. Each digital value within the array of digital values is read and used to control the gray scale level of a pixel on the image. The image thus formed characterizes the cross-section of the workpiece.

The scanner means 15 shown in FIG. 1 has encoder means 46. The encoder 46 has at least one roller such as roller 48 in rotateable contact with the the workpiece surface 47. The encoder means 46 translates linear motion along the operator selected course into an angular signal. Typical couplings include friction and geared means between the roller and the encoder. The encoder means 46 is responsive to the angular signal for providing the distance increment signals to the transmit and receive control means 30.

The transducer means 44 is responsive to the acoustical drive signals or electrical drive pulse on signal line 35 for providing the acoustical pulses or sound pulse to the workpiece surface and for providing the echo signals on signal line 31 in response to the reflected acoustical waves from the workpiece surface.

In a more particular alternative embodiment, the encoder means further comprises a rotateable switch having a rotateable shaft rotateably coupled to the roller. The coupling means is meant to include friction or geared arrangements. The rotateable switch provides the distance increment signals at uniform distance increments along the operator selected course in response to roller 48 rotation induced by roller contact with the workpiece surface 47 and in response to movement of the scanner means 15 along the operator selected course.

The transducer means 44 is typically a purchased component such as a conventional piezoelectric-electric transducer. The transducer is selected to have a narrow or focused beam when pulsed. The acoustical energy in each acoustical pulse is focused into a relatively narrow wedge shaped beam for best operation.

The transducer means 44 in another alternative embodiment has a first transducer responsive to the acoustical drive signals for providing the acoustical pulses and a second transducer responsive to the reflected acoustical waves for providing the echo signals.

Referring to FIG. 1, and in particular to the phantom block 30 enclosing the transmit and receive control means, the transmit control circuit 32 is shown as being responsive via signal line 31 to the distance increment signals from the scanner means 15 for providing a transmit signal on signal line 33 in response to each distance increment signal and for providing an echo interval signal on signal line 37. Each echo interval signal is provided after a first delay interval measured from each acoustical drive transmit signal. The delay is typically performed by a simple adjustable delay circuit (not shown) within the transmit control means block 32, the delay being tailored to the particular scanner. The delay is required to cancel the delay related to moving the acoustical pulse or sound wave from the transducer through the scanner protective coating, across the air gap to the workpiece surface as well as the delay induced by these paths as the echo returns.

The pulser circuit 34 is responsive to the transmit signal on signal line 33 for providing the acoustical drive signals. The pulser is characterized to control the amplitude, shape and duration of the acoustical drive signal transmitted via signal path 35.

Phantom block 30 also contains a sample rate timing circuit 38 coupled to receive the echo interval signal on signal line 37 and an output terminal for providing the column clock signal set on signal line 39.

In a more particular embodiment, the sampling means further comprises: a receiver means 22, an A-D converter means 24, and a temporary memory means such as FIFO 26.

The receiver means 22 is responsive to the echo signals as they arrive on signal line 21. It amplifies the echo signals and conditions the amplified echo signals and provides a receiver signal on signal line 23.

The A-D converter means 24 is responsive to the receiver signal on signal line 23 and to the column clock signal set on signal line 39. The A-D converter converts the amplitude of the receive signal into a digital value for and outputs these digital values on signal line 25 concurrent with each spaced column clock signal. This process results in converting each echo signal into a corresponding column series of digital values. Each value characterizes the amplitude of the echo signal at a time corresponding to a respective column clock signal within the echo interval. FIG. 2B shows the envelope intensity of a received echo signal as it changes within 256 time frames. The A-D converter senses the peak value of this analogue signal and provides a digital value representing the peak value of the echo intensity signal for each of the 256 time frames.

The temporary memory means 26 is typically a 256 by 3 bit FIFO array fabricated from conventional memory devices. The temporary memory means 26 is responsive to the column clock signal set coupled to it on signal line 39 for temporarily storing each of the corresponding column series of digital values from the A-D converter means 24 at a rate corresponding to the clock rate of the column clock signal set. The present part is a Monolithic Memories (MMI) 67401. The FIFO is fabricated from three one by 256K devices. The parts used are required to be fast enough to accommodate the sample rate and the speed of sound in steel.

The speed of sound is about 6500 meters per second in steel. It does not change significantly with temperature or with the frequency of transmission. The 256 samples taken after each transmit pulse are taken over a shorter time interval for steel of thinner wall thickness. The sample rate for 1.0 inch thick steel would typically be close to 20 MHz and the sample rate for 0.5 inch thick steel would typically be near 35 MHz. The FIFO must be capable of accepting data at the highest rate the system anticipates receiving.

The temporary memory means 26 outputs the column series of digital values as data to the storage means 90. As shown in FIG. 2B, the data is formated, clocked and synchronized for storing each column series of digital values as successive column arrays in the storage means 90. Each vertical series of digital values is stored as successive column arrays to form an image array of digital values.

In a more particular alternative embodiment, the temporary memory means 26 is further characterized to output a ready signal on signal line 28 at the conclusion of storing each column series of digital values from the A-D converter means 24. The ready signal is meant to signal that the column series of digital values are stored in the FIFO and available for output as the data to the storage means 90 on signal line 29. It is understood that signal line 29 is meant to represent a parallel bus of three or four signal depending on the resolution selected for the system.

Referring to FIG. 1 the storage means 90 for storing each column series of digital values as successive column arrays to form an image array of digital values further comprises major elements such as digital memory means 85, sample address counter means 82, display address counter means 84, write address logic circuit means 70 and address select logic 86.

The digital memory means 85 is organized to receive and store each column series of digital values as successive column arrays. The preferred embodiment stores each column digital value as a three bit word.

The sample address counter means 82 is responsive the transmit and receive control means via signal line 39 for initialling and incrementing a sample address counter control means to control the location of each successive column series of digital values in the storage means 90. Signal line 39 provides 256 clock pulses in response to each distance increment signal. These clock signals are typically used to increment a row address counter within the sample address counter. Signal line 41 couples a delayed clock signal for each distance increment signal. This clock signal is used by the sample address counter to increment a column address counter within the sample address counter for each distance increment signal.

The display address counter means 84 is responsive via signal line 61 to the display means 50 for controlling the sequence of reading of the contents of the storage means 80 to form an image from the image array of digital values in digital memory array 85. Each digital read controls the gray scale level of a pixel on the image when displayed by the display means 50. The image characterizing the cross-section of the workpiece.

The write address logic circuit means responsive to the ready signal on signal line 28 for interrupting the sampling of the contents of the storage means 80 and for enabling the sample address counter means 82 to control the storage of each successive column series of digital values in the storage means 80 digital memory array 85.

In another more particular alternative embodiment, the sampling means 20 of FIG. 1 receiver means 22 is responsive to the echo signals via signal line 21 for amplifying and conditioning the echo signals from the piezoelectric-electric transducer 44. The receiver is designed to have low noise and to provide a receiver signal on signal line 23.

In this particular embodiment, the A-D converter means 24 responsive to the receiver signal on signal line 23 and to the column clock signal set on signal line 39 for converting the amplitude of the receive signal into a digital value for each spaced column clock signal. The A-D converter provides a column series of digital values, each value corresponding to a particular clock signal within column clock signal set and each value characterizing the amplitude of the echo signal at a time corresponding to a respective column clock signal within the echo interval.

In this embodiment, the temporary memory means 26 is a three (3) by 256 FIFO responsive to the column clock signal set for temporarily storing each of the corresponding column series of digital values from the A-D converter means 24 at a rate corresponding to the clock rate of the column clock signal set. The FIFO then outputs the column series of digital values as data on three wire signal bus 29 to the storage means 80. The data is formated, clocked and synchronized for storing each column series of digital values as successive column arrays in the storage means 80. Each series of digital values is stored as successive column arrays in digital memory array 85 within memory means 80 to form an image array of digital values.

In a particular alternative embodiment, the temporary memory means 26 is further characterized to output a ready signal on signal line 28 at the conclusion of storing each column series of digital values from the A-D converter means 24 to signal that the column series of digital values are stored and available for output as data on three wire bus 29 to the storage means 80.

The storage means 80 for storing each column series of digital values as successive column arrays to form an image array of digital values comprises elements such as digital memory array 85, sample address counter means 82, display address counter means 84, write address logic circuit means 70 and address select logic 86.

The digital memory array 85 receives and stores each column series of digital values as successive column arrays, each digital value being a three bit word. P The sample address counter means 82 is responsive to the transmit and receive control means 30 for initializing and incrementing row and column address counters within the sample address counter control means to control the location of each successive column series of digital values in the storage means 80.

The display address counter means 84 is responsive to the display means 50 for controlling the sequence of reading of the contents of the storage means 80 to format the display data on three wire bus 81. The display data is formated to be compatible with the display means 50 video monitor 90. Each digital value controls the gray scale level of a pixel on the image. The image characterizes the cross-section of the workpiece 49.

The write address logic circuit means 70 is responsive to the ready signal for interrupting the sequence of reading of the contents of the storage means 80 to form the display data and for enabling the sample address counter means 82 to control the storage of each successive column series of digital values in the storage means 80.

The address select logic 86 is responsive to the write address block output to interrupt memory operations under the control of the display address counter 84 and to shift control of the memory to write data into memory under the control of the sample address counter 82.

The display means 50 for forming an image from the display data formed from the image array of digital values comprises elements such as video monitor means, timing generator means 60, and image processor means.

Figure 3:
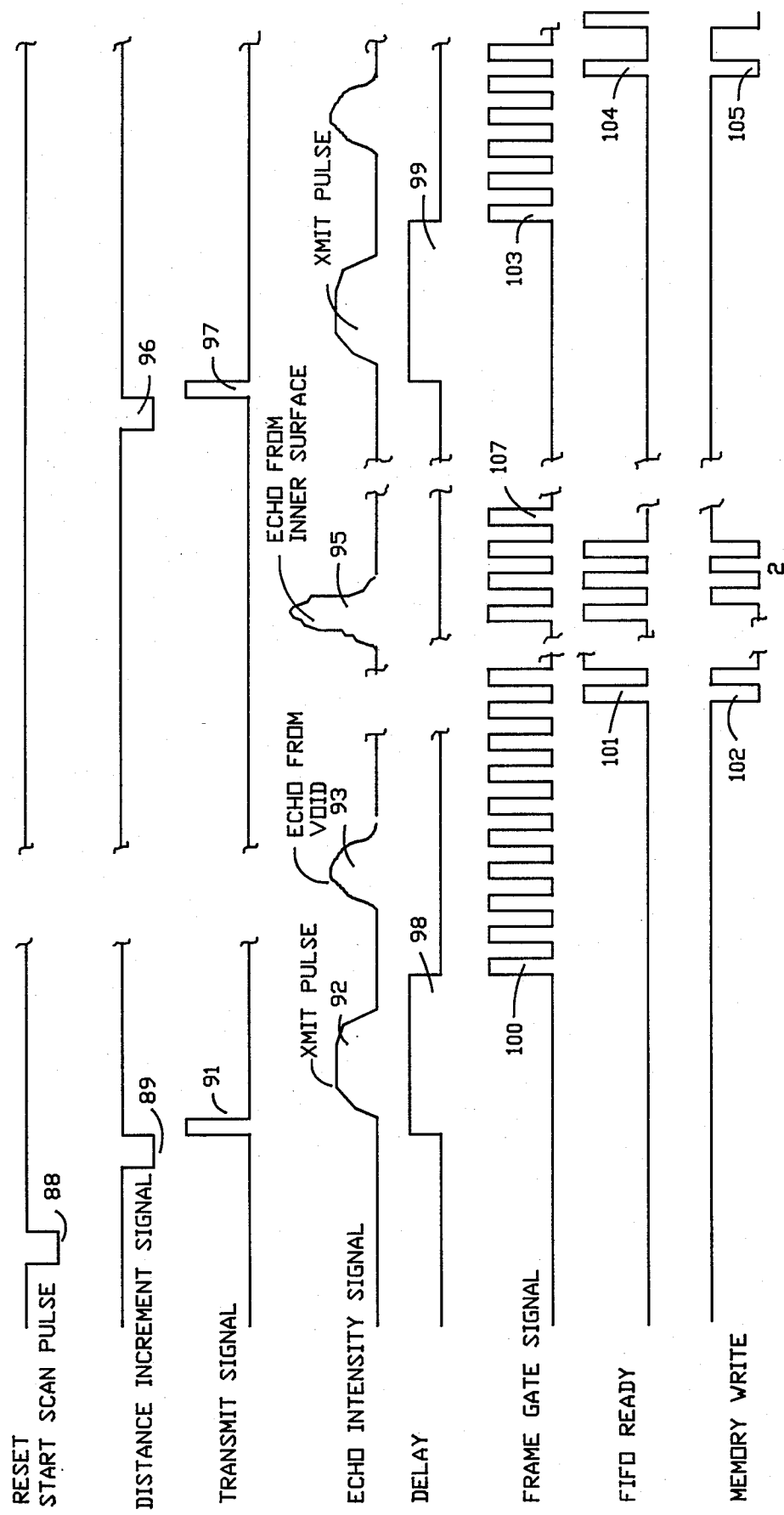
FIG. 3 is a signal timing diagram.

Referring to FIG. 3, recall that information is loaded in a serial fashion vertically into the memory array, the return echo sample values being stored in 256 vertical locations. Adjacent locations contain information resulting from successive transmissions and echo returns at the same depth within the workpiece under test. The data is read out as serial data in a memory row, each row corresponding to a TV MONITOR raster scan line. There are 128 columns of information in the map of data in the memory and each row would typically produce 128 data words per row. In this system, intermediate values are generated from every pair of data values. These intermediates values are generated by taking the sum of adjacent measured values and dividing by two. This process provides 256 values for display for each trace of the TV raster. This function is provided by the AVERAGER LOGIC CIRCUIT block 58 in FIG. 1.

The video monitor means 90 has a synchronous horizontal and vertical deflection frequency and imaging means for the display of a video signal. A conventional TV monitor is meant to be included in those available for use.

The timing generator means 60 provides at least first and second clock signals, each having a respective frequency characterized to synchronize the video monitor means horizontal and vertical deflection frequency, and at least a third clock signal characterized to have a frequency equal to the number of the columns in the image array times the horizontal frequency. The preferred embodiment has 128 columns in the image array.

The image processor means has elements within phantom block 52 and is responsive to the third clock signal and to the display data on bus 81 for filtering and converting the data into a display compatible video signal.

The video monitor means 90 is responsive to at least the first and second clock signals on signal lines 54 and 56 and the video signal on signal line 67 for displaying the image characterizing the cross-section of the workpiece.

The D-A Converter 64 receives digital data as 3 bit words on input bus 63 and converts it to an analogue control signal compatible with the video monitor input requirements.

The TV Format Generator is synchronized by the horizontal and vertical sinc signals on signal lines 54 and 56 to pass the video signal from its input to its output during even raster scans and to allow alpha numeric data to be impressed on the video during alternate raster scans.

In another alternative embodiment, the temporary memory means 26 is characterized to be responsive to the first clock signal to synchronize the transfer of data to the the storage means 80 with the horizontal retrace of the display means. The digital memory means 80 receives and stores each column series of digital values as successive column arrays in digital memory array 85.

In this embodiment, the sample address counter means 82 is responsive to the transmit and receive control means 30 for initializing and incrementing the sample address counter control means 82 to control the location of each successive column series of digital values in the storage means 80. In addition, the sample address has a column address counter (not shown)

clocked by the distance increment signal and a horizontal address counter (not shown) clocked by the third clock signal.

The display address counter means 84 in this embodiment is responsive to the display means 50 for controlling the sequence of reading of the contents of the storage means 80 to form an image from the image array of digital values. The display address counter has a horizontal address counter clocked by the third clock signal and a column address counter clocked by the first clock signal. Each digital data value is read under control of row and column address counters within the display address counter block 84.

SYSTEM OPERATION

A preferred embodiment of the invention system characterized by FIG. 1 is presently in production and is enjoying commercial success in that there are no known portable instruments available that can perform the same function. The present system is known as the TMI-150.

The purpose of the system is to non-destructively provide an image of the cross section of a solid workpiece. The present system is capable of imaging the cross section of metal such as steel having a thickness of more than 0.050 inches. Steel having this thickness is imaged on the top half of a five inch screen and conveniently portrays the thickness of the metal over which the scanner is passed to within plus or minus 0.010 inches. These characteristics are expected to improve as faster circuitry becomes available.

Referring to FIG. 1, the transducer sequence is started by a pulse from encoder 42. The encoder is driven by a friction wheel 48 in surface contact with the surface 47 of a workpiece 49 under test. The encoder provides a series of pulses such as distance increment signal 89 in FIG. 2 as the scanner 15 is moved on the test surface. The pulses issue at uniformly spaced distances as the friction wheel is rolled on the surface. The linear distance traveled by the friction wheel on the surfaces between pulses corresponds to the width of each column or vertical frame of information depicted on the video display. The scan is made vertically or normal to the surface of the workpiece 47.

Figure 4D:
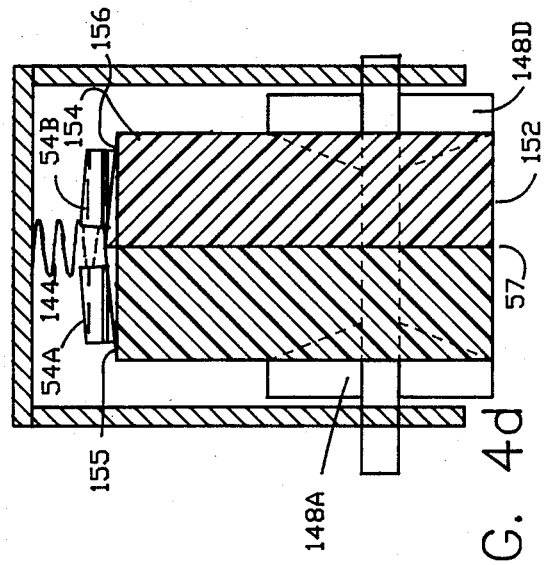
Figure 4C:
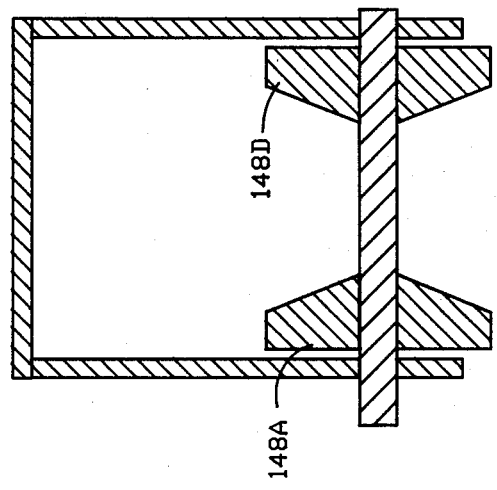

Transducer 44 in scanner 15 can be used for sending and receiving or a split pair of transducers can be used. FIGS. 4a, b, c and d show views of a an alternative embodiment of a scanner in which reference numbers 54A and 54B represent transducer elements for transmitting and receiving. The transducers are shown in FIG. 4d atop a two section support 53 of TORLON 4203. TORLON is a trademark of AMACO and is available from Industrial Plastics Supply Co. located in Anaheim, Calif. The transducers such as 54A and 54B have been purchased from several sources including AEROTECH of Los Angeles, PANOMETRICS, and from the model 100 series manufactured by ADVANCED MECHANICAL SYSTEMS INC. of Wallingford, Conn.

The transducer is typically pulsed with a sawtooth voltage wave form rich in harmonics. It is filtered to achieve a particular range of frequencies at the transducer itself. The sawtooth pulse to the transducer is characterized as a negative going voltage spike of very short duration provided by drive circuitry in the PULSER 34 block of FIG. 1. The transducer presents a capacitive load to the drive circuit.

Figure 4B:
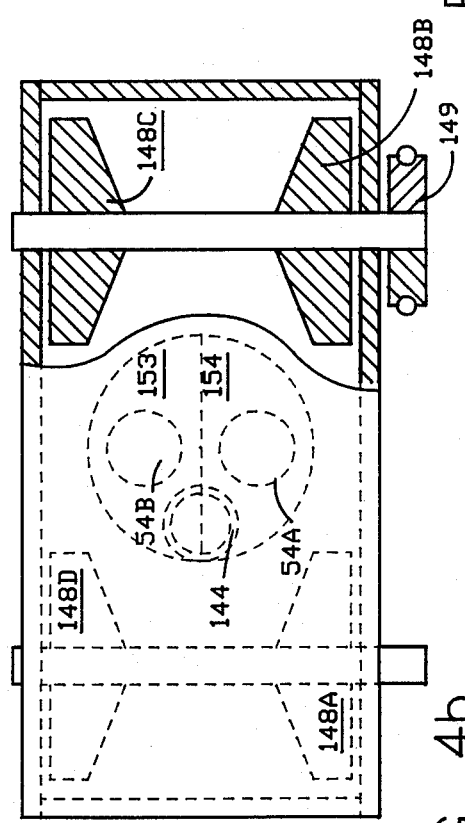
Figure 4A:
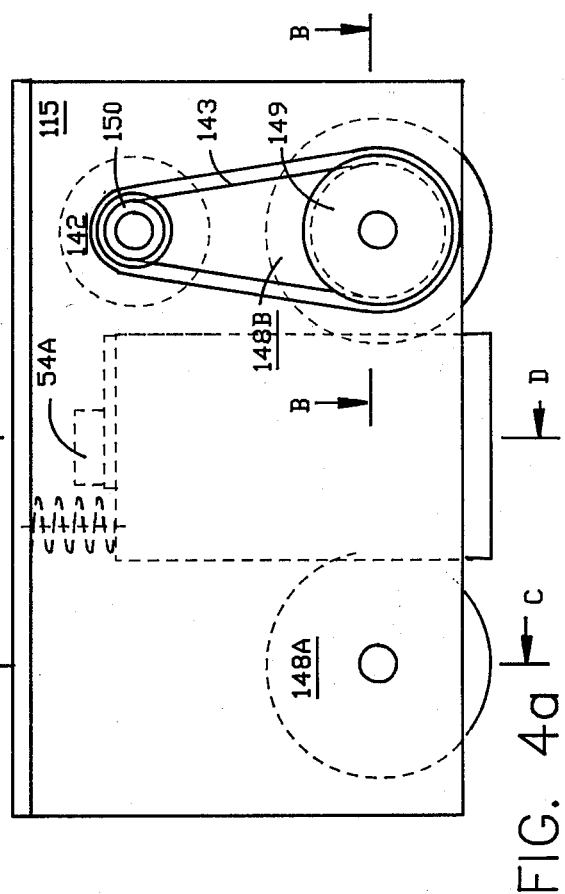
FIG. 4a is a side elevation view of a scanner.

FIG. 4b is a part elevation part sectional view of FIG. 4a taken along line B—B in which the two sections of the support 153 and 154 are shown in phantom through the top surface of the scanner. Spring 144 provides a restoring force to hold the support against the workpiece surface. Friction wheel 148 is equipped with an external grooved drive wheel that provides drive to the shaft of the encoder 142 via O-Ring 143 and encoder O-Ring retainer drive wheel 150.

FIG. 4d shows the surface of the supports 155, 156 on which the transducers 54A and 54B are mounted cut at an angle with the vertical interface 57 of the two sections of the torlon support 153, 154. The angle is selected to focus the energy transmitted by the transmitting transducer, such as 54A within a circle having a diameter of approximately 0.25 inches at a point axially aligned with vertical interface 57 and approximately 2 inches beneath the support bottom surface 152. A typical angle for the transducer mounting surface is 85 degrees measured from interface 57. FIG. 4a is a side elevation of the scanner 115 supported by rollers 148A and 148B. In this characterization, roller 148B serves as the above referenced friction wheel and drives the encoder 142 via O-RING 143. Spring 144 is shown in phantom providing a restoring force to transducer support 153, 154 to hold the transmitting surface of support 53 against the surface of the workpiece (not shown). FIG. 4b shows the cross-section of rollers 148A AND 148C. The support 153 is shown in phantom. A retaining means is not shown; however, this would typically be provided by a sleeve coupled to the scanner housing. Wheel 148D is shown in phantom. FIG. 4c represents FIG. 4a sectioned along line C—C. Rollers 148A and 148D are shown on a bearing shaft.

FIGS. 4a through 4d do not show circuit connections to the transducers as the connections required, the location of the receiver 22 and pulser 34 is a matter of design choice, good practice requiring that the receiver be located as close to the transducer as possible and if possible in the scanner 115.

Referring to FIG. 2A, subsequent to acoustical pulse transmittal from the transducer 44, the system switches to a receive mode and monitors the transducer echo signal for a received echo signal. The transmitted and received transducer acoustic pulses are represented schematically by 45 and 47 respectively.

FIG. 2B shows that the invention system stores all of the data that returns as a series of samples. 256 Samples from each echo return represented by echo intensity signal values are shown being sent to FIFO 26 and stored in a column array. The system repeats the process for 128 encoder pulses storing each set of 256 echo intensity signal values in successive column arrays as the scanner traverses the workpiece. The granularity of the display in this embodiment is therefore 128 frames of vertical intensity information, each vertical frame having 256 values of intensity information characterizing the intensity of the echo return at successively deeper depths in the workpiece. The 128 pulses are spaced along the operator selected track of the system. The 256 samples of each echo are taken as each echo return is received from the surface of the workpiece surface.

The 256 samples are displayed by the preferred embodiment on one-half (½) of the height of a standard TV Video screen. There are 512 lines per frame. The second half of the video display is reserved for video data relating to the operator controls from the keyboard. The keyboard is used by the operator to command alternate scan depths, expanded scale, log depth display and other alternate features relating to the display of data.

The memory is organized into a series of 128 columns and 256 rows. The columns are in the vertical plane and the rows are in the horizontal plane. The SAMPLE RATE TIMING block 30 signals a row address counter in the SAMPLE ADDRESS COUNTER BLOCK 82 to increment one count down in the horizontal plane. The memory is loaded by columns and read out by rows. FIG. 3 characterizes the relationship. The 256 rows correspond to approximately one half of the TV Screen raster.

The WRITE ADDRESS BLOCK 70 is used to shift data words memory from the FIFO to the Digital Memory. It operates at a compatible TV frame rate to control a row and column address counters in the SAMPLE ADDRESS COUNTER block 92 to accommodate the column by column loading of data words from the FIFO into memory and to accommodate row and column counters in the DISPLAY ADDRESS COUNTER 84 to permit row by row read out of the mapped data in memory. As the contents of the FIFO is written into a column array of memory locations, the readout is interrupted. The necessity for interruption is minimized by synchronizing the the load of new data into memory with TV Blanking time or with scan retrace. The viewer sees vertical slide of video information added to the picture as the FIFO is unloaded each time.

Signal line 28 carries a signal that indicates that the FIFO is ready to shift out its contents. The signal is passed to the WRITE ADDRESS BLOCK 70. Signal line 51 is the address write enable signal to DIGITAL MEMORY. As the address lines for a particular memory location go low, data is passed from the output of the FIFO 26 to that memory location. Signal line 51 is coupled to every IC in the memory. The signal on line 51 is different from the signal on line 61 in that the signal on 51 is a command to begin to shift information from the FIFO to the memory. The signal on line 28 is a ready indication. The FIFO chips each have their own FIFO READY or FULL and a FIFO LOAD signal line. As the column and row addresses are clocked to address successive column addresses in the memory block, information is transferred as signal line 51 goes low. Data is not transferred if the write enable signal on signal line 51 is not low.

The WRITE ADDRESS BLOCK 70 is a separate address scheduling or interrupt system. The row and column address counters in the DISPLAY ADDRESS COUNTER 84 are strobing memory at all times for digital display data in a screen line by screen line format. The memory is row sampled by taking 128 from sequential locations, each location having the same row address. The row address counter is then incremented and the process is repeated for the next row of 128 samples. Each row of 128 is enhanced up to 256 samples by use of the an averaging algorithm referenced.

In an alternative embodiment, controlled by a selector switch, (not shown), the process is made to continue for an indefinite number of pulses. In this configuration, new information obtained via scanner readings is used to continuously replace the oldest information on the video display as the scanner continues to move past the point at which the 128th encoder pulse issued.

Referring to FIG. 3, a delay represented by delay pulse 98 is introduced between the transmit interval that starts with transmit signal 91 and the start of the receive interval that begins with the first frame gate signal 100 of 256 frame gate signals to accommodate the time required for the transmitted sound to get from the transducer mounting surface 155, 156 to the workpiece and the time required for sound to travel from the workpiece surface back to the transducer. This delay is typically made adjustable to accommodate the structural features of the scanner. The delay circuit is typically a part of the transmit control block 32 shown in FIG. 1 and is of a conventional design, such as one using an inexpensive NE555 integrated timer circuit. Without this delay, no intensity information would be received until the leading edge of the reflected echo returned to the scanner transducer 44 resulting in blank or black depth indication on the video display.

The reset start scan pulse 88 is typically a manually initiated pulse signaled by the operator to clear all registers, counters and memory in preparation for motion of the scanner. A first and subsequent distance increment signal are characterized by pulses 89 and 96 generated by ENCODER 42 in response to motion of scanner 115. These pulses are followed by respective transmit signals 91 and 97. The echo intensity signal transmit pulse 92 represents the RECEIVER 22 response to the acoustical pulse. The echo void signal 93 represent the receiver response to an echo from within the workpiece, such as a bubble or void or crack and inner surface echo 95 represents a response from the far surface of the workpiece.

Frame gate signals 100 through 107 are shown characterizing an interval encompassing the time required to monitor all returning echoes until the far echo 95 is received. FIFO READY signal 101 is shown occurring after several frame gate signals since time is required to allow the digitized value of the echo intensity signal from the A-D CONVERTER 24 to propagate from the input of the FIFO 26 to its output latches. The memory write signal enables the memory to transfer information from the FIFO output to the SAMPLE ADDRESS COUNTER 82 designated memory locations during horizontal retrace time via the address select logic circuit 86.

The received sound wave is converted to an electrical signal by a piezoelectric-electric transducer such as 54B, and amplified by a receiver such as receiver 22 to form an echo intensity signal such as 93, 95 which is fed to an A-D converter comprised of a bank of six comparatores. Each comparator in the bank is set to switch at a successively higher threshold level. As a frame gate signal occurres, the status of all comparator outputs are sampled simultaneously. The eight outputs of the comparatores are coupled to eight inputs of a conventional TTL priority encoder (not shown).

The priority encoder provides a binary word output on three signal lines for each frame gate signal to the FIFO 26. Each of these three bit data words correspond to the highest input being received of the input string of lines. The highest output possible on these signal lines is a 110 or a six. If a three is on, the output will be 011. The state of the comparator outputs characterize via the priority encoder, a word of data that is read out and stored for each of 256 equally spaced time intervals for each sound transmission. 128 Sound transmissions are provided for each scan of the head as it is transported across the surface of the workpiece.

The three bit word provides eight possible states starting with all three bits being off or reset. The preferred embodiment system uses seven of the available eight states of the three bit word to characterize seven possible shades of gray of a video pixel on a particular scan line at a horizontal location corresponding to the respective encoder pulse.

The time going and coming represents the depth or distance and the amplitude of the return signal characterizes the presence or absence of a fault. If there is no imperfection in the medium, then no reflected wave occurs and the signal remains low in amplitude. Shades of gray or black at points in the video display represent a defect or obstruction to the wave at a point intermediate to the opposite wall boundary.

In an alternative embodiment, the amplitude of the video signal is monitored by gray threshold detection circuits (not shown) having a predetermined threshold. Such detection circuits can be used to alert an operator of a fault condition in a workpiece without activation of the video monitor. An LM339 threshold detector circuit would typically be adjusted to provide an alarm signal as the gray video signal penetrates a predetermined limit. The signal on signal line 65 might typically be monitored by the comparator circuit to control a conventional audio oscillator driving a speaker or piezoelectric audio transducer selected to provide an audible alarm. Operation of the system in this mode allows the operator to use the system without the video monitor thereby reducing the power required for operation and extending the time available for portable field operation on rechargeable batteries.

The display means is represented in FIG. 1 by the blocks within phantom block 50. The TV TIMING GENERATOR block 60 is typically a conventional camera sync generator integrated circuit such as a Fairchild 3262BCD, a National 5321 or a Hatachi MM5321. These circuits operate with a conventional group of related discrete components such as a 14.318 MHz crystal to provide precision sync and control signals on signal lines 61, 54 and 69. The display address counter block 84 embodies a column and row address counter (not shown), these counters being synchronized via the sinc signals on signal line 61 to constantly read the contents of memory 85 out on signal line 81 in sequential row format compatible with the VIDEO MONITOR 90 scanning raster.

The contents of the memory is mapped onto the VIDEO MONITOR's display one row after another for both odd and even fields. The monitor is synchronized to the arrival of the data by the composite conventional sync signals on signal line 54. The read out of the memory is continuous and is only interrupted during flyback or vertical retrace via a control signal from WRITE ADDRESS block 70 to ADDRESS SELECT LOGIC block 86 to allow the SAMPLE ADDRESS COUNTER 82 row and column address counters (not shown to control the loading of data from the FIFO 26 in column format. The operation of the information up-date process is governed by the concurrence of frame gate signals and a monitor flyback or blanking pulse.

The AVERAGER LOGIC CIRCUIT 58 receives data from signal line 51 and functions to average pairs of row data words to produce an averaged data value in between each pair of row data words. By operation of the AVERAGER LOGIC CIRCUIT 58, 128 data words for each raster scan are converted into 256 separate values as the trace moves across the monitor.

The D-A CONVERTER 64 is a standard TTL part. This function block includes a one-of-sixteen encoder. It receives four bits in parallel, one bit of which is null and three bits from the AVERAGER LOGIC CIRCUIT 58 on signal line 59. The received data word causes one of sixteen possible outputs to go low. A pull-up resistor chain (not shown) having a resistor divider node controlled by each of sixteen output transistors is switched by one of sixteen lines out of the one-of-sixteen encoder to provide the required scaled video signal on signal line 65 to the TV FORMAT GENERATOR 66.

The TV FORMAT GENERATOR BLOCK 66 represents conventional circuitry and logic for passing the video signal on signal line 65 to the VIDEO MONITOR 90 signal input line 67, or for replacing the video information with formated alpha numeric information from ROM memory to provide control setting and status information on the lower half of the TV MONITOR screen.

It is my belief that the foregoing description of a preferred embodiment of my invention is presented in sufficient detail to enable one skilled in the art to make and use the invention without undue experimentation. However, in so doing, it is not my intent to restrict or limit my invention to the details I have provided. Other elements may be substituted and improvements or modifications may be made to the forgoing. These substituted, added elements or improvements when combined will become apparent, to those skilled in the art, upon reading this specification as combinations expressing or containing the teachings presented in this specification. Accordingly, it is respectfully requested that my invention be broadly construed within the full spirit and scope of the appended claims.

I claim:

1. An imaging system for non-destructively imaging the cross-section of a workpiece, said cross-section being taken substantially orthogonal to the surface of said workpiece along an operator selected course on said surface, said image system comprising:

a scanner means for providing a series of acoustical pulses in response to a corresponding series of acoustical drive signals; for receiving reflected acoustical waves from said workpiece surface and providing an echo signal corresponding to the received acoustical waves for each acoustical pulse; and for providing a series of distance increment signals at substantially equal incremental distances in response to motion of said scanner means on said workpiece surface along said operator selected course;

a transmit and receive control means responsive to each distance increment signal for providing an acoustical drive signal and a column clock signal set comprising a predetermined number of consecutive spaced column clock signals, the duration of said column clock signal set characterizing an echo interval as the time required for said acoustical waves resulting from each acoustical pulse to move through said workpiece and return to said scanner means;

sampling means responsive to said column clock signal set for converting each said echo signal into a corresponding column series of digital values, each value characterizing the amplitude of said echo signal at time corresponding to a respective column clock signal within said echo interval;

storage means for storing each column series of digital values as successive column arrays to form an image array of digital values, each digital value having a corresponding column and row address, and for reading and outputting said image array of digital values as display data in display compatible format;

display means for forming an image from said display data formed from said image array of digital values, each digital value controlling the gray scale level of a pixel on said image, said image characterizing the cross-section of said workpiece.

2. The imaging system of claim 1 wherein said scanner means further comprises:

an encoder means having at least one roller in rotatable contact with said said workpiece surface for translating linear motion along said operator selected course into an angular signal to said encoder, said encoder means being responsive to said angular signal for providing said distance increment signals to said transmit and receive control means; and a transducer means responsive to said acoustical drive signals for providing said acoustical pulses and for providing said echo signals in response to said reflected acoustical waves.

3. The imaging system of claim 2 wherein said encoder means further comprises a rotatable switch having a rotatable shaft rotatable coupled to said roller, said rotatable switch providing said distance increment signals at uniform distance increments along said operator selected course in response to roller rotation induced by roller contact with said workpiece surface and in response to movement of said scanner means on said operator selected course.

4. The imaging system of claim 2 wherein said transducer means is further characterized to focus the acoustical energy in each acoustical pulse into a relatively narrow cone shaped beam.

5. The imaging system of claim 2 wherein said transducer means further comprises at least a first transducer responsive to said acoustical drive signals for providing said acoustical pulses.

6. The imaging system of claim 5 wherein said transducer means further comprises at least a second transducer responsive to said reflected acoustical waves for providing said echo signals.

7. The imaging system of claim 1 wherein said transmit and receive control means 30 further comprises:

a transmit control circuit responsive to said distance increment signals from said scanner means for providing an acoustical drive transmit signal in response to each distance increment signal and for providing an echo interval signal, each echo interval signal being provided after a first delay interval measured from each acoustical drive transmit signal;

a pulser circuit responsive to said transmit signal for providing said acoustical drive signals, and being characterized to control the amplitude, shape and duration of said acoustical drive signal; and a sample rate timing circuit coupled to receive said echo interval signal and an output terminal for providing said column clock signal set.

8. The imaging system of claim 7 wherein said sampling means further comprises:

a receiver means responsive to said echo signals for amplifying and conditioning said echo signals and providing a receiver signal;

an A-D converter means responsive to said receiver signal and to said column clock signal set for converting the amplitude of said receive signal into a digital value for each spaced column clock signal to provide said corresponding column series of digital values, each value characterizing the amplitude of said echo signal at a time corresponding to a respective column clock signal within said echo interval; and a temporary memory means responsive to said column clock signal set for temporarily storing each said corresponding column series of digital values from said A-D converter means at a rate corresponding to the clock rate of said column clock signal set and for outputting said column series of digital values as data to said storage means, said data being formated, clocked and synchronized for storing each column series of digital values as successive column arrays in said storage means;

whereby each vertical series of digital values is stored as successive column arrays to form an image array of digital values.

9. The imaging system of claim 8 wherein said temporary memory means is further characterized to output a ready signal at the conclusion of storing each column series of digital values from said A-D converter means 24 to signal that said column series of digital values are stored and available for output as said data to said storage means.

10. The imaging system of claim 7 wherein said storage means for storing each column series of digital values as successive column arrays to form an image array of digital values further comprises:

digital memory means for receiving and storing each column series of digital values as successive column arrays;

sample address counter means responsive said transmit and receive control means for initializing and incrementing a sample address counter control means to control the location of each successive column series of digital values in said storage means 90;

display address counter means responsive to said display means for controlling the sequence of reading of the contents of said storage means to form said display data, said display data being formated to be compatible with said display means, each digital value controlling the gray scale level of a pixel on said image, said image characterizing the cross-section of said workpiece; and write address logic circuit means responsive to said ready signal for interrupting said sequence of reading of the contents of said storage means to form said display data and for enabling said sample address counter means to control the storage of each successive column series of digital values in said storage means.

11. The imaging system of claim 1 wherein said sampling means further comprises:

a receiver means responsive to said echo signals for amplifying and conditioning said echo signals and providing a receiver signal;

an A-D converter means responsive to said receiver signal and to said column clock signal set for converting the amplitude of said receive signal into a digital value for each spaced column clock signal to provide said corresponding column series of digital values, each value characterizing the amplitude of said echo signal at a time corresponding to a respective column clock signal within said echo interval; and a temporary memory means responsive to said column clock signal set for temporarily storing each said corresponding column series of digital values from said A-D converter means at a rate corresponding to the clock rate of said column clock signal set and for outputting said column series of digital values as data to said storage means, said data being formated, clocked and synchronized for storing each column series of digital values as successive column arrays in said storage means;

whereby each vertical series of digital values is stored as successive column arrays.

12. The imaging system of claim 11 wherein said a temporary memory means is further characterized to output a ready signal at the conclusion of storing each column series of digital values from said A-D converter means to signal that said column series of digital values are stored and available for output as said data to said storage means.

13. The imaging system of claim 12 wherein said storage means for storing each column series of digital values as successive column arrays to form an image array of digital values further comprises:

digital memory means for receiving and storing each column series of digital values as successive column arrays;

sample address counter means responsive said transmit and receive control means for initializing and incrementing a sample address counter control means to control the location of each successive column series of digital values in said storage means;

display address counter means responsive to said display means for controlling the sequence of reading of the contents of said storage means to form an image from said image array of digital values, each digital value controlling the gray scale level of a pixel on said image, said image characterizing the cross-section of said workpiece; and write address logic circuit means responsive to said ready signal for interrupting said sampling of the contents of said storage means and for enabling said sample address counter means to control the storage of each succesive column series of digital values in said storage means.

14. The imaging system of claim 11 wherein said display means for foring an image from said display data formed from said image array of digital values further comprises:

video monitor means having a synchronizable, horizontal and vertical deflection frequency and imaging means for the display of a video signal;

timing generator means for providing a first clock signal to synchronize said video monitor horizontal frequency and a second clock signal to synchronized said video monitors vertical frequency and at least a third clock signal characterized to have a frequency equal to the number of said columns in said image array times said horizontal frequency;

image processor means responsive to said third clock signal and to said display data for filtering and converting said display data into a display compatible video signal; and said video monitor means being responsive to at least said first and second clock signals and said video signal for displaying said image characterizing the cross-section of said workpiece; and wherein said temporary memory means being further characterized to be responsive to said first clock signal for synchronize the transfer of data to said said storage means with the horizontal retrace of said display means, said digital memory means 80 for receiving and storing each column series of digital values as successive column arrays;

and wherein said digital memory means is further characterized to have a sample address counter means responsive said transmit and receive control means for initializing and incrementing a sample address counter control means to control the location of each successive column series of digital values in said storage means, said sample address counter having a column address counter clocked by said distance increment signal and a horizontal address counter clocked by said third clock signal, and display address counter means responsive to said display means for controlling the sequence of reading of the contents of said storage means to form an image from said image array of digital values, said display address counter having a horizontal address counter clocked by said third clock signal and a column address counter clocked by said first clock signal, each digital data value being read under control of said row and column address counters controlling the gray scale level of a pixel on said image, said image characterizing the cross-section of said workpiece; and write address logic circuit means responsive to said ready signal for interrupting said sampling of the contents of said storage means and for enabling said sample address counter means to control the storage of each successive column series of digital values in said storage means.

15. The imaging system of claim 1 wherein said storage means for storing each column series of digital values as successive column arrays to form an image array of digital values further comprises:

digital memory means for receiving and storing each column series of digital values as successive column arrays;

sample address counter means responsive said transmit and receive control means for initializing and incrementing a sample address counter control means to control the location of each successive column series of digital values in said storage means;

display address counter means responsive to said display means for controlling the sequence of reading of the contents of said storage means to form an image from said image array of digital values, each digital value controlling the gray scale level of a pixel on said image, said image characterizing the cross-section of said workpiece; and write address logic circuit means responsive to said ready signal for interrupting said sampling of the contents of said storage means and for enabling said sample address counter means to control the storage of each successive column series of digital values in said storage means.

16. The imaging system of claim 1 wherein said display means for forming an image from said display data formed from said image array of digital values further comprises:

video monitor means having a synchronizable, horizontal and vertical deflection frequency and imaging means for the display of a video signal;

timing generator means for providing at least first and second clock signals, each having a respective frequency characterized to synchronize said video monitor means synchronizable, horizontal and vertical deflection frequency, and at least a third clock signal characterized to have a frequency equal to the number of said columns in said image array times said horizontal frequency;

image processor means responsive to said third clock signal and to said display data for filtering and converting said data into a display compatible video signal; and said video monitor means being responsive to at least said first and second clock signals and said video signal for displaying said image characterizing the cross-section of said workpiece.

17. The imaging system of claim 1 wherein said display means further comprises:

means for signaling the presence of a predetermined echo signal.

18. The imaging system of claim 17 wherein said means for signaling the presence of a predetermined echo signal further comprises audio signaling means for indicating the presence of said predetermined echo to said operator.

19. An imaging system for non-destructively imaging the cross-section of a workpiece, the cross-section of the workpiece being taken orthogonal to the surface of the workpiece along an operator selected course on the surface, the imaging system comprising:

a hand-held scanner means for transmitting and receiving acoustical signals to and from the workpiece surface and for providing distance increment signals in response to movements of the scanner means on the workpiece surface;

a transmit and receive control means responsive to each distance increment signal for providing an acoustical drive signal and a frame gate signal set;

a sampling means responsive to the column clock signal set for receiving and converting each the echo signal into a corresponding column series of digital values, each value characterizing the amplitude of the echo signal at time corresponding to a respective column clock signal within the echo interval characterized by the frame gate signal set; and a stoage means for storing each column series of digital values as successive column arrays to form an image array of digital values, and means for maping the array of digital values in the means onto a video monitor display.

* * * * *

REEXAMINATION CERTIFICATE (3086th)

United States Patent [19]
Rutherford

[11] B1 4,625,557
[45] Certificate Issued Dec. 31, 1996

[54] ACOUSTICAL IMAGING SYSTEM

[75] Inventor: Jerry Rutherford, Anaheim, Calif.

[73] Assignee: Lora E. Rutherford, Lake Barrington, Ill.

Reexamination Request:
No. 90/004,046, Nov. 30, 1995

Reexamination Certificate for:
Patent No.: 4,625,557
Issued: Dec. 2, 1986
Appl. No.: 703,315
Filed: Feb. 20, 1985

[51] Int. Cl.$^6$ ................................................. G01N 29/06
[52] U.S. Cl. ........................................................ 73/635
[58] Field of Search .......................... 73/660, 606, 609, 73/618, 635, 637, 638, 639, 607; 364/507, 508, 413.25; 128/660.07, 660.08, 660.09, 660.10, 661.02

[56] References Cited

U.S. PATENT DOCUMENTS

| | | | |
|---|---|---|---|
| 3,798,961 | 3/1974 | Flambard et al. | 73/637 |
| 3,820,063 | 6/1974 | Sexton et al. | 367/84 |
| 3,844,164 | 10/1974 | Romere et al. | 73/637 |
| 3,964,296 | 6/1976 | Matzuk | 73/607 |
| 3,988,922 | 11/1976 | Clark et al. | 73/637 |
| 4,106,346 | 8/1978 | Matzuk | 73/614 |
| 4,141,347 | 2/1979 | Green et al. | 128/660.05 |
| 4,197,749 | 4/1980 | Mezrich et al. | 73/625 |
| 4,218,923 | 8/1980 | Triplett et al. | 73/623 |
| 4,226,122 | 10/1980 | Lund et al. | 73/609 |
| 4,325,256 | 4/1982 | Horn | 73/607 |
| 4,333,346 | 6/1982 | Renzel | 73/606 |
| 4,359,904 | 11/1982 | Engle et al. | 73/620 |
| 4,381,787 | 5/1983 | Hottinger | 73/620 |
| 4,383,448 | 5/1983 | Fujimoto et al. | 73/637 |
| 4,417,475 | 11/1983 | Okazaki | 73/606 |
| 4,455,872 | 6/1984 | Kossoff et al. | 73/618 |
| 4,541,064 | 9/1985 | Livingston | 73/620 |
| 4,596,145 | 6/1986 | Smith et al. | 73/626 |
| 4,605,938 | 8/1986 | Matsuno et al. | 347/176 |
| 4,836,026 | 6/1989 | P'an | 73/620 |
| 4,885,761 | 12/1989 | Sones et al. | 378/197 |

OTHER PUBLICATIONS

Highlights of a Breadboard Demonstration of a Portable Seawater Component Integrity Measuring Instrument, Jul. 1978.

Buchanan, R. W., et al., Ultrasonic Flow Plotting Equipment—A New Concept for Industrial Inspection, Nondestructive Testing, Sep.–Oct. 1955, pp. 17–25.

Gleicher, N. J., et al., Determining Variability of Wall Thickness Measurements During Ultrasonic Inspection of Shipsystem Components, Materials Evaluation, Dec. 1978, pp. 47–52.

Kessler, L. W., et al., Acoustic Microscopy—1979, Proceedings of the IEEE, vol. 67, No. 4, Apr. 1979, pp. 526–535.

Fitzpatrick, G., Seismic Imaging by Holography, Proceedings of the IEEE, vol. 67, No. 4, Apr. 1979, pp. 536–553.

Mueller, R. K., et al., Reconstructive Tomography and Applications to Ultrasonics, Proceedings of the IEEE, vol. 67, No. 4, Apr. 1979, pp. 567–587.

(List continued on next page.)

*Primary Examiner*—Christine K. Oda

[57] ABSTRACT

An imaging system for non-destructively imaging the cross-section of a workpiece is taught. The image provided portrays the cross-section of the workpiece taken orthogonal to the surface of the workpiece along an operator selected course on the surface. The imaging system comprises: a scanner means for transmitting and receiving acoustical signals and for providing distance increment signals; a transmit and receive control means responsive to each distance increment signal for providing an acoustical drive signal and a column clock signal set. A sampling means is provided that is responsive to the column clock signal set for converting each the echo signal into a corresponding column series of digital values, each value characterizing the amplitude of the echo signal at time corresponding to a respective column clock signal within the echo interval. A storage means is provided for storing each column series of digital values as successive column arrays to form an image array of digital values. The storage means also reads and maps the image array of digital values as display data onto a video monitor.

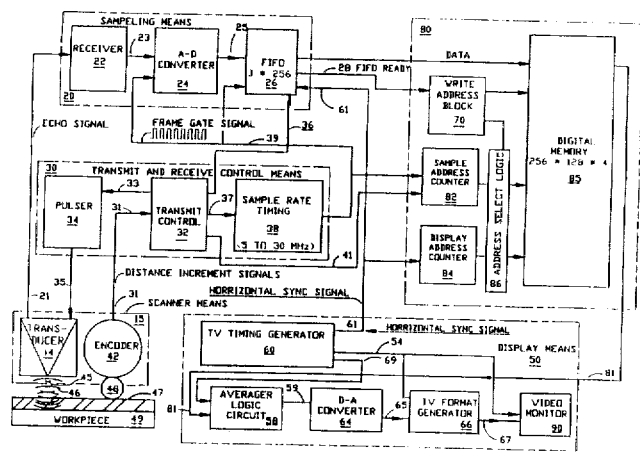

OTHER PUBLICATIONS

Fry, F. J., Biological Effects of Ultrasound—A Review, Proceedings of the IEEE, vol. 67, No. 4, Apr. 1979, pp. 604–619.

Havlice, J. F., et al., Medical Ultrasonic Imaging: An Overview of Principles and Instrumentation, Proceedings of the IEEE, vol. 67, No. 4, pp. 620–639, Apr. 1979.

Deter, R. L., et al., A Survey of Abdominal Ultrasound Scanners: The Clinician's Point of View, Proceedings of the IEEE, vol. 67, No. 4, pp. 664–671, Apr. 1979.

Hamlin, D. R., et al., Program for Field Validation of the Synthetic Aperture Focusing Technique for Ultrasonic Testing (SAFT UT), Quarterly Progress Report, Jun. 1981.

Gebhardt, W., et al., Defect Reconstruction and Classification by Phased Arrays, Materials Evaluation, vol. 40, No. 1, Jan. 1982, pp. 90–95.

Adams, T. E., Micro–Images from Ultrasound, Materials Evaluation, vol. 40, No. 1, Jan. 1982.

Automated Ultrasonic Weld Inspection Services for Scots Offshore Fabrication Yard, NDT International, Apr. 1982, p. 101.

Moore, M. J., et al., Real–Time Signal Processing in an Ultrasonic Imaging System, Materials Evaluation, Aug. 1982, pp. 976–981.

Wade, J. C., et al., Specification for the Digital Recording of Ultrasonic Signals, Sep. 1982.

Peterson, D. K., et al., Real–Time NDE of Flaws Using a Digital Acoustic Imaging System, Nov. 1982, pp. 1256–1262.

B–Scan Displays of Ultrasonic Time–of–Flight Diffraction Tests of Compact Tension Specimens, United Kingdom Atomic Energy Authority, Harwell, Jan. 1984.

Busse, L. J., et al., Review and Discussion of the Development of Synthetic Aperture Focusing Technique for Ultrasonic Testing (SAFT–UT), NRC Public Document NUREG/CR–3625 PNL–4957, Mar. 1984.

Corrosion Abstracts, vol. 24, No. 5, Sep.–Oct. 1985, pp. 346–348.

Kino, G. S., Acoustic Waves: Devices, Imaging, and Analog Signal Processing, 1987, pp. 222–225, 255–258, 313–317, 591–592.

Hall, T. E., et al., The SAFT–UT Real–Time Inspection System—Operational Principles and Implementation, NCR Public Document NUREG/CR–5075 PNL–6413, Jun. 1988.

McMaster, R. C., Nondestructive Testing Handbook, Society for Nondestructive Testing, vol. II, New York, 1959, pp. 43.30–43.49; 43.46–43.53; 46.1–46.5; 47.28–47.39.

Holmes, J., Ultrasonic Contact Scanner for Diagnostic Application, The American Journal of Medical Electronics, Oct.–Dec. 1965, pp. 147–152.

Engelbart, D., et al., A research center for augmenting human intellect, AFIS—Conference Proceedings, vol. 33, Fall Computer Conference, 1968, pp. 395–410.

Grohs, B., et al., Characterization of Flaw Location, Shape, and Dimensions with the ALOK System, Materials Evaluation/40/Jan. 1982, pp. 84–89.

Nondestructive Inspection and Quality Control, Metals Handbook, 8th Edition, vol. 11, American Society for Metals, Handbook Committee, 1976, pp. 170–175.

Anonymous, New Images Born to the Electronic Age, Materials/40/Jan. 1982, pp. 36–38.

Clark, J. P. et al., A Remotely Controlled, Inservice Inspection System, Invention Disclosure, General Electric, Apr. 12, 1974.

Krautkramer, J., et al., Ultrasonic Testing of Materials (selected excerpts), New York, 1977, pp. 197–202; 344–345; 390–391; 521–523.

Lancaster, D., The Cheap Video Cookbook, 1978, pp. 13–17.

Maginness, M., Methods and Terminology for Diagnostic Ultrasound Imaging Systems, Proceedings of the IEEE, vol. 67, No. 4, Apr. 1979, pp. 641–653.

Ophir, J., et al., Digital Scan Converters in Diagnostic Ultrasound Imaging, Proceedings of the IEEE, vol. 67, No. 4, Apr. 1979, pp. 654–664.

Schmitz, V., et al., A New Ultrasonic Imaging System, Technical Paper, Materials Evaluation/40/Jan. 1982, pp. 101–108.

Cecco, V. S., et al., Ultrasonic Time–of–flight B–Scan Presentation, United Kingdom Atomic Energy Authority, Harwell, Apr. 1983.

Sllesenger, T. A., An Introduction to the Concepts and Hardware Used for Ultrasonic Time–of–flight Data Collection and Analysis, United Kingdom Atomic Energy Authority, Harwell, May 1985.

Fleming, M., et al., (Amdata Systems, Inc.), Proposal for Development of Automated Mobile Bridge Insepction System (AMBIS), prepared for U.S. Department of Transportation Federal Highway Administration, Washington, D.C., Proposal 83–19, 1983.

Brasel, D., The Use of Ultrasonic Testin as a Diagnostic Method in Pregnancy, Materials Evaluation, 40, Jan. 1982, pp. 20–24.

Glenn, W. E., et al., High Resolution Ultrasonic System for Real–Time Video Imaging of Internal Flaws, Materials Evaluation, 40, Jan. 1982, pates 96–100.

News/Products & Services Section, Materials Evaluation, 40, Jan. 1982, pp. 53–55.

Neumann, R. K., et al., Hardware Equipment for Realtime–Determination of Data Gained from A–Scans by Automatic Ultrasonic Inspection for Flaw–Reconstruction by ALOK, 1981 Ultrasonic Symposium Proceedings, Chicago, IL, Oct. 14–16, 1981, Chicago, IL, vol. 2, pp. 985–988.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 to 19 is confirmed.

* * * * *

REEXAMINATION CERTIFICATE (3519th)

United States Patent [19]
Rutherford

[11] B2 4,625,557
[45] Certificate Issued May 26, 1998

[54] ACOUSTICAL IMAGING SYSTEMS

[75] Inventor: Jerry Rutherford, Anaheim, Calif.

[73] Assignee: Lora E. Rutherford, Lake Barrington, Ill.

Reexamination Request:
No. 90/004,554, Feb. 14, 1997

Reexamination Certificate for:
Patent No.: 4,625,557
Issued: Dec. 2, 1986
Appl. No.: 703,315
Filed: Feb. 20, 1985

Reexamination Certificate B1 4,625,557 issued Dec. 31, 1996

[51] Int. Cl.$^6$ .................................................. G01N 29/06
[52] U.S. Cl. .................................................. 73/635
[58] Field of Search .......................... 73/660, 606, 609, 73/618, 635, 637, 638, 639, 607; 364/507, 308, 413.35; 600/445, 446, 441, 443

[56] References Cited

U.S. PATENT DOCUMENTS

| | | | |
|---|---|---|---|
| 3,798,961 | 3/1974 | Flambard et al. | 73/637 |
| 3,820,063 | 6/1974 | Sexton et al. | 367/84 |
| 3,844,164 | 10/1974 | Romere et al. | 73/637 |
| 3,964,296 | 6/1976 | Matzuk | 73/67.5 |
| 3,988,922 | 11/1976 | Clark et al. | 73/67.8 |
| 4,106,346 | 8/1978 | Maztuk | 73/614 |
| 4,141,347 | 2/1979 | Green et al. | 128/2 |
| 4,197,749 | 4/1980 | Mezrich et al. | 73/625 |
| 4,218,923 | 8/1980 | Triplett et al. | 73/623 |
| 4,226,122 | 10/1980 | Lund et al. | 73/609 |
| 4,317,370 | 3/1982 | Glenn | 73/620 |
| 4,325,256 | 4/1982 | Horn | 73/607 |
| 4,333,346 | 6/1982 | Renzel | 73/606 |
| 4,359,904 | 11/1982 | Engle et al. | 73/620 |
| 4,381,787 | 5/1983 | Hottinger | 73/620 |
| 4,383,448 | 5/1983 | Fujimoto et al. | 73/637 |
| 4,417,475 | 11/1983 | Okazaki | 73/606 |
| 4,455,872 | 6/1984 | Kossoff et al. | 73/618 |
| 4,541,064 | 9/1985 | Livingston | 73/637 |
| 4,596,145 | 6/1986 | Smith et al. | 73/626 |
| 4,605,938 | 8/1986 | Matsuno et al. | 347/176 |
| 4,836,026 | 6/1989 | P'an | 73/620 |
| 4,885,761 | 12/1989 | Jones et al. | 378/197 |

OTHER PUBLICATIONS

McMaster, R.C., *Nondestructive Testing Handbook*, Society for Nondestructive Testing, vol. II, New York, 1959, pp. 43.30–43.49; 43.46–43.53; 46.1–46.5; 47.28–47.39.

Holmes, J., *Ultrasonic Contact Scanner for Diagnostic Application*, The American Journal of Medical Electronics, Oct.–Dec. 1965, pp. 147–152.

Engelbart, D., et al., *A research center for augmenting human intellect*, AFIS—Conference Proceedings, vol. 33, Fall Computer Conference, 1968, pp. 395–410.

Mahoon, A. et al., *Computer–Controlled Ultrasonic Testing of Aircraft Structures*, British Journal of NDT, pp. 316–320.

SBDTR–8160 User's Manual, Revision A, Adaptronics Products, Advanced Technologies Division, General Research Corporation (1983), pp. 1–18.

(List continued on next page.)

*Primary Examiner*—Christine K. Oda

[57] ABSTRACT

An imaging system for non-destructively imaging the cross-section of a workpiece is taught. The image provided portrays the cross-section of the workpiece taken orthogonal to the surface of the workpiece along an operator selected course on the surface. The imaging system comprises: a scanner means for transmitting and receiving acoustical signals and for providing distance increment signals; a transmit and receive control means responsive to each distance increment signal for providing an acoustical drive signal and a column clock signal set. A sampling means is provided that is responsive to the column clock signal set for converting each the echo signal into a corresponding column series of digital values, each value characterizing the amplitude of the echo signal at time corresponding to a respective column clock signal within the echo interval. A storage means is provided for storing each column series of digital values as successive column arrays to form an image array of digital values. The storage means also reads and maps the image array of digital values as display data onto a video monitor.

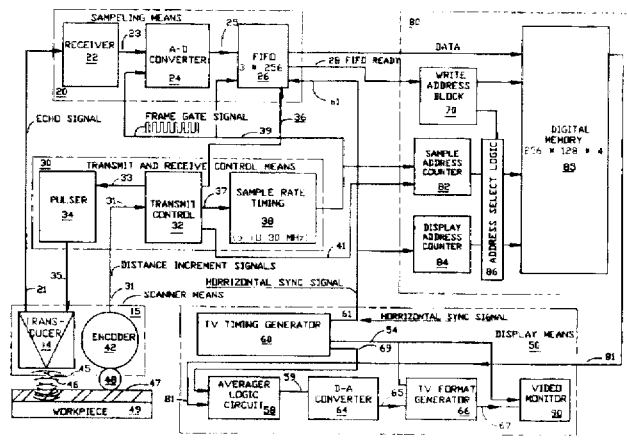

OTHER PUBLICATIONS

Anonymous, *New Images Born to the Electronic Age*, Materials/40/Jan. 1982, pp. 36–38.

Loverne, R. N., et al, *Remote/Auto, Ultrasonic Examination System*, General Electric, Dec. 1975, pp. 1–25.

Krautkramer, J., et al., *Ultrasonic Tesing of Materials* (selected excerpts), New York, 1977, pp. 197–202; 344–345; 390–391; 521–523.

Lancaster, D., *The Cheap Video Cookbook*, 1978, pp. 13–17.

Maginness, M., *Methods and Terminology for Diagnostic Ultrasound Imaging Systens*, Proceedings of the IEEE, vol. 67, No. 4, Apr. 1979, pp. 641–653.

Ophir, J., et al., *Digital Scan Converters in Diagnostic Ultrasound Imaging*, Proceedings of the IEEE, vol. 67, No. 4, Apr. 1979, pp. 654–664.

MetroTek, Ultrasonic Instruments Catalog, May 1979.

Fleming, M., et al. (Amdata Systems, Inc.), *Proposal for Development of Automated Mobile Bridge Insepction System (AMBIS)*, prepared for U.S. Department of Transportation Federal Highway Administration, Washington, D.C., Proposal 83–19.

Brasel, D., *The Use of Ultrasonic Testing as a Diagnostic Method in Pregnancy*, Materials Evaluation 40, (Jan. 1982), pp. 20–24.

Amdata Systems, Inc., *Amdata Amaps 2060*, pp. 1–2.

Adams, "Micro–Images from Ultrasound", *Materials Evaluation*, v 40, No. 1, Jan. 1982.

Buchanan, et al. "Ultrasonic Flow Plotting Equipment—A New Concept for Industrial Inspection", *Nondestructive Testing*, Sep.–Oct. 1955, pp. 17–25.

Busse, et al, "Review and Discussion of the Development of Synthetic Aperature Focusing Technique for Ultrasonic Testing (SAFT–UT)", NRC Public Document, NUREG/CR–3625 PNL–4957, Mar. 1984.

Cecco, et al, *Ultrasonic Time–of–Flight B–ScanPresentation*, United Kingdom Atomic Energy Authority, Harwell, Apr. 1983.

Clark, et al, *A Remotely Controlled, Inservice Inspection System*, Invention Disclosure, General Electric, Apr. 12, 1974.

Deter, et al., "A Survey of Abdominal Ultrasound Scanners: The Clinician's Point of View", *Proceedings of the IEEE*, v. 67, No. 4, Apr. 1979, pp. 664–671.

Fitzpatrick, "Seismic Imaging by Holography", *Proceedings of the IEEE*, v. 67, No. 4, Apr. 1979, pp. 536–553.

Fry, "Biological Effects of Ultrasound—A Review", *Proceedings of the IEEE*, v. 67, No. 4, Apr. 1979, pp. 604–619.

Gebhardt, et al, "Defect Reconstruction and Classification by Phased Arrays", *Materials Evaluation*, v 40, No. 1, Jan. 1982, pp. 90–95.

Glenn, et al, "High Resolution Ultrasonic System for the Real–Time Video Imaging of Internal Flaws", *Materials Evaluation*/40, Jan. 1982, pp. 96–100.

Gleicher, et al, "Determining Variability of Wall Thickness Measurements During Ultrasonic Inspection of Ship System Components", *Materials Evaluation*, Dec. 1978, pp. 47–52.

Grohs, et al. "Characterization of Flaw Location, Shape and Dimensions With the ALOK System", *Materials Evaluation*/40, Jan. 1982, pp. 84–89.

Hall, et al, The Saft–UT Real–Time Inspection System—Operational Principles and Implementation, NRC Public Document, NUREG/CR–5075 PNL–6413, Jun. 1988.

Hamlin, et al, Program for Field Validation of the Synthetic Aperature Focusing Technique for Ultrasonic Testing (SAFT UT), *Quarterly Progress Report*, Jun. 1981.

Havlice, et al, "Medical Ultrasonic Imaging: An Overview of Principles and Instrumentation", *Proceedings of the IEEE*, v. 67, No. 4, Apr. 1979, pp. 620–639.

Kessler, et al., "Acoustic Microscopy—1979", *Proceedings of the IEEE*, v. 67, No. 4, Apr. 1979, pp. 526–535.

Kino, *Acoustic Waves: Devices, Imaging and Analog Signal Processing*, 1987, pp. 222–225, 255–258, 313–317, 591–592. (no month).

Moore, et al, "Real–Time Signal Processing in an Ultrasonic Imaging System", *Materials Evaluation*, Aug. 1982, pp. 976–981.

Mueller, et al. "Reconstructive Tomography and Applications to Ultrasonics", *Proceedings of the IEEE*, v. 67, No.4, Apr. 1979, pp. 567–587.

Neumann, et al. "Hardware Equipment for Realtime–Determination of Data Gained from A–Scans by Automatic Ultrasonic Inspection for Flaw–Reconstruction by ALOK", *1981 Ultrasonic Symposium Proceedings*, Chicago, IL, Oct. 14–16, 1981, v. 2, pp. 985–988.

Peterson, et al, *Real–Time NDE of Flaws Using a Digital Acoustic Imaging System*, Nov. 1982, pp. 1256–1262.

Schmitz, et al. "A New Ultrasonic Imaging System", Technical Paper, *Matrials Evaluation*/40, Jan. 1982, pp. 101–108.

Sllesenger, "An Introduction to the Concepts and the Hardware Used for Ultrasonics Time–of–Flight Data Collection and Analysis", United Kingdom Atomics Energy Authority, Harwell, May 1985.

Wade, et al. *Specification for the Digital Recording of Ultrasonic Signals*, Sep. 1982.

Automated Ultrasonic Weld Inspection Services for Scots Offshore Fabriacation Yard, *NDT International*, Apr. 1982, p. 101.

"B–Scan Displays of Ultrasonic Time–of–Flight Diffraction Tests of Compact Specimens", United Kingdom Atomic Energy Authority, Harwell, Jan. 1984.

*Corrosion Abstracts*, v. 29, No. 5, Sep.–Oct. 1985, pp. 346–348.

*Highlights of a Breadboard Demonstration of a Portable Seawater Component Integrity Measuring Instrument*, Jul. 1978.

"News/Products & Services Section", *Materials Evalution*/40, Jan. 1982, pp. 53–55.

"Nondestructive Inspection and Quality Control", *Metals Handbook*, 8th Ed., v. 11, American Society for Metals, Handbook Committee, 1976, pp. 170–175.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 to 19 is confirmed.

* * * * *